(12) United States Patent
Murao et al.

(10) Patent No.: US 7,307,184 B2
(45) Date of Patent: Dec. 11, 2007

(54) PROCESSES FOR PREPARING OXAZOLIDINONE DERIVATIVES OF β-HYDROXYETHLAMINE COMPOUNDS AND FOR PREPARING β-HYDROXYETHLAMINE COMPOUNDS

(75) Inventors: Hiroshi Murao, Hyogo (JP); Koki Yamashita, Kobe (JP); Toshihiro Takeda, Takasago (JP); Yasuyoshi Ueda, Himeji (JP)

(73) Assignee: Kaneka Corporation, Osaka-shi (JP)

( * ) Notice: Subject to any disclaimer, the term of this patent is extended or adjusted under 35 U.S.C. 154(b) by 438 days.

(21) Appl. No.: 10/478,439

(22) PCT Filed: May 23, 2002

(86) PCT No.: PCT/JP02/04984

§ 371 (c)(1),
(2), (4) Date: Jan. 26, 2004

(87) PCT Pub. No.: WO02/100841

PCT Pub. Date: Dec. 19, 2002

(65) Prior Publication Data

US 2004/0181074 A1    Sep. 16, 2004

(30) Foreign Application Priority Data

May 23, 2001   (JP) .......................... P2001-154084

(51) Int. Cl.
C07C 269/00   (2006.01)
C07C 269/06   (2006.01)

(52) U.S. Cl. ...................... 560/115; 564/487; 564/488; 564/503

(58) Field of Classification Search ..................... None
See application file for complete search history.

(56) References Cited

U.S. PATENT DOCUMENTS 4,294,966 A    10/1981   Zergenyi 5,670,653 A    9/1997   Hilpert
6,140,506 A  * 10/2000   Baba et al. ................. 548/221

FOREIGN PATENT DOCUMENTS

| JP | 32-002675 B1 | 5/1957 |
| JP | 55-145650 | 11/1980 |
| JP | 55-145650 A | 11/1980 |
| JP | 9-169744 | 6/1997 |
| WO | WO 02/00601 A1 | 1/2002 |

OTHER PUBLICATIONS

Langolois et al. Eur. J. Org. Chem. 1999, 3483-3488.*
Parrodi et al. Tetrahedron Asymmetry, 1997, 8, 1075-1082.*
Foglia et al. J. Org. Chem, 1988, 33, 766-771.*
Adv. Carbohydr. Chem. Biochem, (1967), vol. 22, p. 109.
Adv. Carbohydr. Chem. Biochem, (1967), vol. 22, p. 139-141.

* cited by examiner

Primary Examiner—Yvonne Eyler
Assistant Examiner—Yevgeny Valenrod
(74) Attorney, Agent, or Firm—Foley & Lardner LLP

(57) ABSTRACT

The present invention provides a process of starting from N-alkoxycarbonyl-ethylamine compounds having a leaving group at the β-position to prepare oxazolidinone derivatives of β-hydroxyethylamine compounds having an inverted steric configuration at the β-position carbon, which comprises introducing a step of treating in contact with water with heating under acidic to neutral conditions into the process. Also, the present invention provides a process of starting from N-alkoxycarbonyl-ethylamine compounds having a leaving group at the β-position to prepare β-hydroxyethylamine compounds having an inverted steric configuration at the β-position carbon, which comprises subjecting the oxazolidinone derivatives prepared as described above to a step of treating in contact with water under basic conditions.

17 Claims, No Drawings

PROCESSES FOR PREPARING OXAZOLIDINONE DERIVATIVES OF β-HYDROXYETHLAMINE COMPOUNDS AND FOR PREPARING β-HYDROXYETHLAMINE COMPOUNDS

TECHNICAL FIELD

The present invention relates to a process for preparing oxazolidinone derivatives of β-hydroxyethylamine compounds. Also, the present invention relates to a process for preparing β-hydroxyethylamine compounds in a high quality and a high yield.

The oxazolidinone derivatives of β-hydroxyethylamine compounds in the present invention are not limited to particular ones. They have a 2-oxazolidinone-substructure, and hydrogen atoms on the 4-position and 5-position carbon atoms thereof may be optionally substituted or unsubstituted. Also, the β-hydroxyethylamine compounds in the present invention are not limited to particular ones. They have a β-hydroxyethylamine-substructure, and hydrogen atoms on the α-position and β-position carbon atoms thereof may be optionally substituted or unsubstituted.

The oxazolidinone derivatives of β-hydroxyethylamine compounds obtained by the process according to the present invention can be easily derivatized into corresponding β-hydroxyethylamine compounds by contacting with water (hydrolyzing) under basic conditions, and therefore, the former derivatives are known as equivalents of β-hydroxyethylamine compounds.

The above β-hydroxyethylamine compounds, in particular, optically active β-hydroxyethylamine compounds are utilized, for example, in the production of chiral catalysts for enantio-selective cyclopropanation, reduction, hydrosilylation, Diels-Alder reaction or the like [Angew.Chem., vol. 103, p. 556 (1991)]. Also, in an asymmetric-induction reaction utilizing optically active β-hydroxyethylamine compounds, for example, in the synthesis of a bicyclic lactam by a condensation reaction with a γ- or δ-ketocarboxylic acid [Tetrahedron, vol. 47, p. 9503 (1991)], remarkably high enantio-selectivity or diastereo-selectivity is often observed.

Furthermore, optically active β-hydroxyethylamine compounds are found in a variety of natural products including aminoglycoside antibiotics, and many groups of compounds having a high physiological activity are reported as peptide isosteres. Among others, a β-carboxy-β-hydroxy-α-benzyl-ethylamine compound, that is, 3-amino-2-hydroxy-4-phenylbutyric acid is a useful compound as an intermediate for medicines: (2S,3R)-isomer (i.e. threo-isomer) of the compound can be led, for example, to an immunostimulating anticancer agent, Bestatin [J.Antibiotics, vol. 29, p. 600 (1976)]; on the other hand, (2S,3S)-isomer (i.e. erythro-isomer) of the compound can be led, for example, to a HIV protease inhibitor, KNI-227 (JP-A-05/170722). Accordingly, a process for the stereo-selective production of the above β-hydroxyethylamine compounds, in particular, optically active β-hydroxyethylamine compounds has a great significance.

BACKGROUND ART

To date, a variety of methodologies have been intensively investigated for the processes of synthesizing optically active β-hydroxyethylamine compounds, in particular, optically active β-hydroxyethylamine compounds having a desired steric configuration, or their equivalents (i.e. oxazolidinone derivatives of the β-hydroxyethylamine compounds). A process of converting optically active β-hydroxyethylamine compounds into their enantiomers or diastereomers may be mentioned as one of the methodologies [JP-A-09/169,744; JP-A-55/145650; Adv.Carbohydr. Chem.Biochem., vol. 22, p. 109 (1967)].

As one example of the production by this methodology, a process of converting N-alkoxycarbonyl-ethylamine compounds having a leaving group at the β-position, which are obtained by converting a hydroxyl group of optically active β-hydroxyethylamine compounds into a leaving group, into oxazolidinone derivatives of β-hydroxyethylamine compounds having an inverted steric configuration at the β-position carbon is known [Adv.Carbohydr.Chem.Biochem., vol. 22, p. 139 (1967)].

If the oxazolidinone derivatives of β-hydroxyethylamine compounds obtained by this process are contacted with a base, without isolation and purification up to a pure or almost pure form from the operational and/or economical viewpoint in the industrial production, for example, if the derivatives are supplied to a further derivatization under basic conditions, however, there arise problems such as the secondary production of impurities as a side reaction and the decrease of the yield. More particularly, for example, if the derivatives are derivatized into β-hydroxyethylamine compounds by contacting with water under basic conditions, impurities are apt to be produced secondarily and the yield tends to decrease. Accordingly, there is a strong need for establishment of a production process of oxazolidinone derivatives of β-hydroxyethylamine compounds suitable for contact with a base, which process is economically advantageous and is suitable for an industrial production.

In view of the above circumstances, the object of the present invention was to provide a process for preparing oxazolidinone derivatives of β-hydroxyethylamine compounds which is economically advantageous and is suitable for an industrial production, and thereby, to provide a process for preparing β-hydroxyethylamine compounds in a high quality and a high yield which is economically advantageous and is suitable for an industrial production.

DISCLOSURE OF THE INVENTION

The present inventors have intensively investigated in order to solve the above problems. Thus, in a process of starting from the above N-alkoxycarbonyl-ethylamine compounds having a leaving group at the β-position to prepare oxazolidinone derivatives of β-hydroxyethylamine compounds having an inverted steric configuration at the β-position carbon, they have intensively investigated as to the inhibition of the above impurities secondarily produced when the resultant oxazolidinone derivatives of β-hydroxyethylamine compounds are contacted with a base (for example, when the oxazolidinone derivatives are further derivatized, for example into β-hydroxyethylamine compounds by contacting with water, under basic conditions).

As a result, they found that components responsible for the above impurities secondarily produced when the oxazolidinone derivatives are contacted with a base can be made harmless by introducing a step of treating with heating in contact with water under acidic to neutral conditions, into the process of starting from N-alkoxycarbonyl-ethylamine compounds having a leaving group at the β-position to prepare oxazolidinone derivatives of β-hydroxyethylamine compounds having an inverted steric configuration at the β-position carbon. They also found that subsequent derivatization of the oxazolidinone derivatives under basic conditions brings about the inhibition of the secondary production of the impurities and the derivatization in a high quality and a high yield becomes possible. The present inventions were accomplished on the basis of the above findings.

Accordingly, the first invention of the present inventions relates to a process of starting from N-alkoxycarbonyl-ethylamine compounds having a leaving group at the β-position to prepare oxazolidinone derivatives of β-hydroxy-ethylamine compounds having an inverted steric configuration at the β-position carbon, which comprises:

converting the N-alkoxycarbonyl-ethylamine compounds having a leaving group at the β-position into the oxazolidinone derivatives of β-hydroxyethylamine compounds having an inverted steric configuration at the β-position carbon under non-aqueous conditions, and then carrying out a step of treating in contact with water in a molar amount above 5-fold with heating to above 40° C. under acidic to neutral conditions; or subjecting the N-alkoxycarbonyl-ethylamine compounds having a leaving group at the β-position to a step of treating in contact with water in a molar amount above 5-fold with heating to above 40° C. under acidic to neutral conditions.

Also, the second invention of the present inventions relates to a process of starting from N-alkoxycarbonyl-ethylamine compounds having a leaving group at the β-position to prepare β-hydroxyethylamine compounds having an inverted steric configuration at the β-position carbon, which comprises:

converting the N-alkoxycarbonyl-ethylamine compounds having a leaving group at the β-position into oxazolidinone derivatives of β-hydroxyethylamine compounds having an inverted steric configuration at the β-position carbon under non-aqueous conditions, then carrying out a step of treating in contact with water in a molar amount above 5-fold with heating to above 40° C. under acidic to neutral conditions, and then carrying out a step of treating in contact with water under basic conditions; or subjecting the N-alkoxycarbonyl-ethylamine compounds having a leaving group at the β-position to a step of treating in contact with water in a molar amount above 5-fold with heating to above 40° C. under acidic to neutral conditions, and then carrying out a step of treating in contact with water under basic conditions.

BEST MODE FOR PRACTICING THE INVENTION

Hereinafter, the present invention is described in more detail.

More specifically, the present invention relates to a process for preparing oxazolidinone derivatives of β-hydroxyethylamine compounds represented, for example, by the following general formula (1):

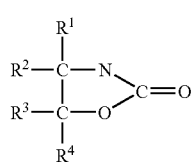

(1)

wherein $R^1$, $R^2$, $R^3$ and $R^4$, independently from each other, represent a hydrogen atom, a substituted or unsubstituted alkyl group, a substituted or unsubstituted aryl group, a substituted or unsubstituted aralkyl group, a substituted or unsubstituted acyl group, a substituted or unsubstituted carboxyl group, a substituted or unsubstituted carbamoyl group, a substituted or unsubstituted amidino group, a cyano group or the like, or two to four of $R^1$ to $R^4$, taken together, represent a substituted or unsubstituted, polyvalent alkyl group or the like;

(hereinafter, simply also referred to as oxazolidinone derivatives)

which comprises introducing a step of treating in contact with water in a molar amount above 5-fold with heating to above 40° C. under acidic to neutral conditions, into a step of converting N-alkoxycarbonyl-ethylamine compounds having a leaving group at the β-position, which have a steric configuration at the β-position carbon reverse to that of the above oxazolidinone derivatives and are represented, for example, by the following general formula (2):

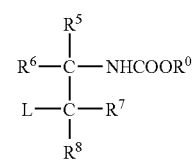

(2)

wherein $R^0$ represents a substituted or unsubstituted alkyl group having 1 to 30 carbon atoms, a substituted or unsubstituted aryl group having 6 to 30 carbon atoms, or a substituted or unsubstituted aralkyl group having 7 to 30 carbon atoms;

$R^5$ represents $R^1$, or a group capable of leading to $R^1$;
$R^6$ represents $R^2$, or a group capable of leading to $R^2$;
$R^7$ represents $R^3$, or a group capable of leading to $R^3$;
$R^6$ represents $R^4$, or a group capable of leading to $R^4$;
$R^1$, $R^2$, $R^3$ and $R^4$ are as defined above; and
L represents a leaving group;

(hereinafter, simply also referred to as N-alkoxycarbonyl-ethylamine compounds)

into the oxazolidinone derivatives represented by the above formula (1) to obtain oxazolidinone derivatives of β-hydroxyethylamine compounds having an inverted steric configuration at the β-position carbon.

Also, the present invention relates to a process for preparing β-hydroxyethylamine compounds represented, for example, by the following general formula (3):

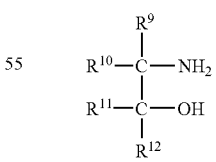

(3)

wherein $R^9$ represents $R^1$, or a group derived from $R^1$;
$R^{10}$ represents $R^2$, or a group derived from $R^2$;
$R^{11}$ represents $R^3$, or a group derived from $R^3$;
$R^{11}$ represents $R^4$, or a group derived from $R^4$;
$R^{12}$ represents $R^4$, or a group derived from $R^4$; and
$R^1$, $R^2$, $R^3$ and $R^4$ are as defined above;

(hereinafter, simply also referred to as β-hydroxyethylamine compounds)

which comprises subjecting the oxazolidinone derivatives obtained by the above process to a step of treating in contact with water under basic conditions.

The above $R^1$, $R^2$, $R^3$ and $R^4$, independently from each other, represent a hydrogen atom, a substituted or unsubstituted alkyl group, a substituted or unsubstituted aryl group, a substituted or unsubstituted aralkyl group, a substituted or unsubstituted acyl group, a substituted or unsubstituted carboxyl group, a substituted or unsubstituted carbamoyl group, a substituted or unsubstituted amidino group, a cyano group or the like, or two to four of $R^1$ to $R^4$, taken together, represent a substituted or unsubstituted, polyvalent alkyl group or the like.

The above substituted or unsubstituted alkyl group is not limited to a particular one, and includes monovalent organic groups which are obtainable by removing one hydrogen atom from a substituted or unsubstituted, saturated aliphatic hydrocarbon having 1 to 30 carbon atoms or a substituted or unsubstituted, unsaturated aliphatic hydrocarbon having 2 to 30 carbon atoms. The monovalent organic groups obtainable by removing one hydrogen atom from a substituted or unsubstituted, saturated aliphatic hydrocarbon having 1 to 30 carbon atoms include, for example, a methyl group, a carbamoylmethyl group, a chloromethyl group, an ethyl group, a carbamoylethyl group, a methylthioethyl group, a propyl group, an isopropyl group, a guanidinopropyl group, an isobutyl group, a sec-butyl group, a 4-aminobutyl group, a 5-aminopentyl group, a cyclohexylmethyl group, a phenylthiomethyl group, a benzyloxymethyl group, a 5-imidazolylmethyl group, a 3-indolylmethyl group or the like. The monovalent organic groups obtainable by removing one hydrogen atom from a substituted or unsubstituted, unsaturated aliphatic hydrocarbon having 2 to 30 carbon atoms include a vinyl group, a 1-propenyl group, a 2-propenyl group, a 2-propynyl group, a 2-butenyl group, a 1,3-butadienyl group, a 2-penten-4-ynyl group, a hexynyl group or the like.

The above substituted or unsubstituted aryl group is not limited to a particular one, and includes monovalent organic groups which are obtainable by removing one hydrogen atom attached to the ring of a substituted or unsubstituted aromatic hydrocarbon having 6 to 30 carbon atoms or a substituted or unsubstituted aromatic heterocycle having 1 to 30 carbon atoms. The monovalent organic groups obtainable by removing one hydrogen atom attached to the ring of a substituted or unsubstituted aromatic hydrocarbon having 6 to 30 carbon atoms include, for example, a phenyl group, a p-chlorophenyl group, a p-fluorophenyl group, a p-methoxyphenyl group, a 1-naphthyl group, a 2-naphthyl group or the like. The monovalent organic groups obtainable by removing one hydrogen atom attached to the ring of a substituted or unsubstituted aromatic heterocycle having 1 to 30 carbon atoms include, for example, a 2-pyridyl group, a 2-oxazolyl group or the like.

The above substituted or unsubstituted aralkyl group is not limited to a particular one, and includes monovalent organic groups which are obtainable by removing one hydrogen atom from a side hydrocarbon chain of a substituted or unsubstituted aromatic hydrocarbon having 7 to 30 carbon atoms. Specifically, they include, for example, a benzyl group, a p-hydroxybenzyl group, a p-methoxybenzyl group, a phenethyl group, a styryl group, a 2-phenylethynyl group, a 2-phenylpropyl group, a 3-phenylpropyl group, a cinnamyl group or the like.

The above substituted or unsubstituted acyl group is not limited to a particular one, and includes a formyl group, a chloroformyl group, an acetyl group, a chloroacetyl group, a propionyl group, a benzoyl group or the like.

The above substituted or unsubstituted carboxyl group is not limited to a particular one, and includes a carboxyl group, a methoxycarbonyl group, an ethoxycarbonyl group, a benzyloxycarbonyl group or the like.

The above substituted or unsubstituted carbamoyl group is not limited to a particular one, and includes a carbamoyl group, a dimethylaminocarbonyl group or the like.

The above substituted or unsubstituted amidino group is not limited to a particular one, and includes an amidino group, a N-ethyl-N'-methylamidino group, a 2-imidazolin-2-yl group or the like.

The above substituted or unsubstituted polyvalent alkyl group is not limited to a particular one, and includes di- to tetra-valent organic groups which are obtainable by removing two to four hydrogen atoms from a substituted or unsubstituted, saturated aliphatic hydrocarbon having 1 to 30 carbon atoms or from a substituted or unsubstituted, unsaturated aliphatic hydrocarbon having 2 to 30 carbon atoms. Such organic groups include, for example, divalent organic groups obtainable by removing two hydrogen atoms from a substituted or unsubstituted, saturated aliphatic hydrocarbon having 1 to 30 carbon atoms such as a methylene group, an ethylene group, an ethylidene group, a propylene group, an isopropylidene group, a tetramethylene group, a pentamethylene group, a hexamethylene group or the like, or divalent organic groups obtainable by removing two hydrogen atoms from a substituted or unsubstituted, unsaturated aliphatic hydrocarbon having 2 to 30 carbon atoms such as a vinylidene group, a propenylene group, a 2-propynyl group, a 4-pentenylene group or the like organic groups obtainable by replacing some of the carbon atoms of the above-mentioned organic groups by, for example, heteroatoms such as a nitrogen atom, an oxigen atom, a phosphorus atom or a sulfur atom, for example, organic groups such as a 2-oxa-1,3-butanediyl group or a 2-oxa-1,4-butanediyl group are also within a range of selection according to the present invention.

Of the above $R^1$, $R^2$, $R^3$ and $R^4$, organic groups used as $R^1$ and $R^2$ are preferably a substituted or unsubstituted alkyl group, a substituted or unsubstituted aryl group, a substituted or unsubstituted aralkyl group, or a substituted or unsubstituted acyl group, and more preferably a substituted or unsubstituted alkyl group, a substituted or unsubstituted aryl group, or a substituted or unsubstituted aralkyl group. Among others, organic groups constituting a side chain of an amino acid or derivatives thereof are preferably used. Specifically, the organic groups constituting a side chain of an amino acid include, for example, a methyl group, a carbamoylmethyl group, an ethyl group, a carbamoylethylgroup, a methylthioethylgroup, a propyl group, an isopropyl group, a guanidinopropyl group, an isobutyl group, a sec-butyl group, a 4-aminobutyl group, a 5-aminopentyl group, a benzyl group, a p-hydroxybenzyl group, a 5-imidazolylmethyl group, a 3-indolylmethyl group or the like, and the organic groups which are derivatives of a side chain of an amino acid include a phenylthiomethyl group, a benzyloxymethyl group, a cyclohexylmethyl group or the like.

Also, organic groups used as $R^3$ and $R^4$ are preferably a substituted or unsubstituted alkyl group, a substituted or unsubstituted acyl group, a substituted or unsubstituted carboxyl group, a substituted or unsubstituted carbamoyl group, a substituted or unsubstituted amidino group, or a cyano group, and more preferably a substituted or unsubstituted alkyl group, a substituted or unsubstituted acyl group, a substituted or unsubstituted carboxyl group, or a cyano group. More specifically, a cyano group, an unsubstituted carboxyl group (i.e. carboxylic acid), an alkoxycarbonyl group such as a methoxycarbonyl group or an ethoxycarbonyl group, an aralkyloxycarbonyl group such as a benzyloxycarbonyl group (i.e. carboxylic acid ester), or a halomethyl group such as a chloromethyl group may be mentioned, for example.

Furthermore, preference is given when the above $R^1$ and $R^2$, or $R^3$ and $R^4$, or either one of $R^1$ or $R^2$ and either one of $R^3$ or $R^4$, taken together, represent a substituted or unsubstituted divalent organic group. Such a substituted or unsubstituted divalent organic group includes, for example, divalent organic groups such as a substituted or unsubstituted tetramethylene group (1,4-butanediyl group), a 2-oxa-1,3-butanediyl group, or a 2-oxa-1,4-butanediyl group.

Of course, the above organic groups used as $R^1$, $R^2$, $R^3$ and $R^4$ apply to organic groups used as the above $R^5$, $R^6$, $R^7$ and $R^8$ as well as organic groups used as the above $R^9$, $R^{10}$, $R^{11}$ and $R^{12}$.

The combination of the above $R^1$, $R^2$, $R^3$ and $R^4$ is not limited to a particular one. Preference is given when $R^1$ and $R^2$ differ from each other and/or when $R^3$ and $R^4$ differ from each other. More preference is given when either one of $R^1$ or $R^2$ is a hydrogen atom and/or when either one of $R^3$ or $R^4$ is a hydrogen atom. Particular preference is given when either one of $R^3$ or $R^4$ is a hydrogen atom. Of course, the above combination of $R^1$, $R^2$, $R^3$ and $R^4$ applies to the combination of the above $R^5$, $R^6$, $R^7$ and $R^8$ as well as the combination of the above $R^9$, $R^{10}$, $R^{11}$ and $R^{12}$.

In addition, it may be also possible that at least one organic group of the above $R^1$, $R^2$, $R^3$, $R^4$, $R^5$, $R^6$, $R^7$ and $R^8$, or at least one substituent in the organic group is derivatized by side reactions such as a substitution, elimination, decomposition or condensation reaction, in a series of the procedures according to the present invention. For example, a methoxycarbonyl group (carboxylic acid methyl ester) may be derivatized into a carboxyl group (carboxylic acid) during the treatment. However, such a derivatization is within the present invention unless it impairs the essence of the present invention.

The alkoxycarbonyl group in the above
N-alkoxycarbonyl-ethylamine compounds is an urethane-type protecting group for an amino group represented by —COOR⁰. The R⁰ represents a monovalent organic group, and specifically, a substituted or unsubstituted alkyl group having 1 to 30 carbon atoms, a substituted or unsubstituted aryl group having 6 to 30 carbon atoms, or a substituted or unsubstituted aralkyl group having 7 to 30 carbon atoms. The above alkoxycarbonyl group is not limited to a particular one, and may be selected from the urethane-type protecting groups for an amino group as described, for example, in PROTECTIVE GROUPS INORGANIC SYNTHESIS, 2nd ed., JOHN WILLY & SONS publ. (1991). In general, from the viewpoint of an easy handling, an inexpensiveness, a convenient synthesis of substrate compounds and the like, a lower alkoxycarbonyl group having 1 to 4 carbon atoms or a substituted or unsubstituted aralkyloxycarbonyl group having 7 to 10 carbon atoms is preferably used, for example. Among others, a methoxycarbonyl group, an ethoxycarbonyl group, a t-butoxycarbonyl group, a benzyloxycarbonyl group or the like is preferably used, and especially, a methoxycarbonyl group or an ethoxycarbonyl group is preferably used. An ethoxycarbonyl group is most preferably used.

In the N-alkoxycarbonyl-ethylamine compounds (2) having a leaving group at the β-position, L represents a leaving group. The above leaving group L is not limited to a particular one and preferably includes, for example, a sulfonyloxy group, a halosulfinyloxy group or a halogen atom. The above sulfonyloxy group is not limited to a particular one and preferably includes, for example, a lower alkylsulfonyloxy group having 1 to 4 carbon atoms or a substituted or unsubstituted arylsulfonyloxy group having 6 to 10 carbon atoms. The above lower alkylsulfonyloxy group includes, for example, a methanesulfonyloxy group, an ethanesulfonyloxy group or the like, and the above arylsulfonyloxy group includes a p-toluenesulfonyloxy group, an o-, p- or m-nitrobenzenesulfonyloxy group or the like. Among others, a methanesulfonyloxy group is preferably used. The above halosulfinyloxy group includes, for example, a chlorosulfinyloxy group, a bromosulfinyloxy group or the like, and a chlorosulfinyloxy group is particularly preferable. The above halogen atom includes, for example, a chlorine atom, a bromine atom, an iodine atom or the like, and a chlorine atom is particularly preferable.

Next described is a process for preparing N-alkoxycarbonyl-ethylamine compounds having a leaving group at the β-position which are starting materials for the process according to the present invention.

The process for preparing N-alkoxycarbonyl-ethylamine compounds is not limited to a particular one, and various processes may be used. However, as exemplified in the section of background art, a process of converting a hydroxyl group of a corresponding N-alkoxycarbonyl-β-hydroxyethylamine compound into the above leaving group is generally used. When converting a hydroxyl group of a N-alkoxycarbonyl-β-hydroxyethylamine compound into the above leaving group, any of known leaving group-introducing agents may be used without any limitation.

If the leaving group is a sulfonyloxy group, a corresponding sulfonyl halide compound is preferably reacted as a leaving group-introducing agent. In general, inexpensive and easily available sulfonyl chloride compounds are preferably used as the above sulfonyl halide compound. Among others, methanesulfonyl chloride, ethanesulfonyl chloride, benzenesulfonyl chloride, p-toluenesulfonyl chloride, nitrobenzenesulfonyl chloride or the like is preferably used, and especially, methanesulfonyl chloride is preferably used. The amount of the above sulfonyl halide compounds used is not limited to a particular range, and they are usually used in a molar amount of 1 to 10-fold, preferably in a molar amount of 1 to 5-fold, and more preferably in a molar amount of 1 of 2-fold, relative to the N-alkoxycarbonyl-β-hydroxyethylamine compounds.

Also, in order to progress the above reaction with sulfonyl halide compounds smoothly, the reaction may be carried out in the coexistence of a base. The base is not limited to a particular one and amines, particularly tertiary amines may be preferably used. The above amines are not limited to a particular one and include triethylamine, diisopropylethylamine pyridine or the like. From the viewpoint of practical use, inexpensive bases are preferable and generally triethylamine is preferably used. The amount of the above amines used is not limited to a particular range, and they are usually used in a molar amount of 1 to 20-fold, preferably in a molar amount of 1 to 5-fold, and more preferably in a molar amount of 1 to 3-fold, relative to the N-alkoxycarbonyl-β-hydroxyethylamine compounds. The reaction temperature can not be defined uniformly and is usually from −20° to 80° C., preferably from −10° to 50° C.

In the introduction of the above leaving group into the N-alkoxycarbonyl-β-hydroxyethylamine compounds, if the leaving group is a halosulfinyloxy group or a halogen atom, thionyl halides are preferably used for the reaction as a leaving group-introducing agent. Usually, inexpensive and easily available thionyl chloride is preferably used as the above thionyl halides. The amount of the above thionyl halides used is not limited to a particular range, and they are usually used in a molar amount of 1 to 10-fold, preferably in a molar amount of 1 to 5-fold, and more preferably in a molar amount of 2 to 3-fold, relative to the N-alkoxycarbonyl-β-hydroxyethylamine compounds. The reaction temperature can not be defined uniformly and is usually from −20° to 120° C., preferably from 0° to 80° C.

Reaction solvents used for the introduction of the above leaving group are not limited to a particular one, if they are essentially inert to the leaving group-introducing agents such as the above sulfonyl halide compounds or the above thionyl halides. Examples of the reaction solvents include, for example, aliphatic hydrocarbons such as hexane or heptane; aromatic hydrocarbons such as toluene or xylene; halogenated hydrocarbons such as methylene chloride or chloroform; ethers such as tetrahydrofuran, 1,4-dioxane or t-butyl methyl ether; aliphatic acid esters such as methyl acetate, ethyl acetate or isopropyl acetate; aprotic polar solvents such as acetonitrile, N,N-dimethylformamide or dimethyl sulfoxide. Among others, the above aromatic hydrocarbons, the above ethers, or the above aliphatic acid esters are preferably used. Toluene is a particularly preferable aromatic hydrocarbon, tetrahydrofuran is a particularly preferable ether, and ethyl acetate is a particularly preferable aliphatic acid ester. These solvents may be used alone or in a mixture of two or more solvents. Besides, if the reaction mixture of the N-alkoxycarbonyl-β-hydroxyethylamine compounds and the above sulfonyl halides or thionyl halides is fluid (for example, they are in a solution state), the above reaction solvents are not necessarily needed.

The N-alkoxycarbonyl-ethylamine compounds having a leaving group at the β-position synthesized by the above process or the other processes may be isolated and/or purified by a conventional method such as extraction, crystallization, distillation, chromatography or the like. However, from the operational and/or economical viewpoint in the industrial production, the products may be used in the production process according to the present invention as they are, without isolation and/or purification by the above conventional method. In this case, the above N-alkoxycarbonyl-ethylamine compounds synthesized by the above process or the like may be occasionally converted into the above oxazolidinone derivatives subsequently under reaction conditions of such a process. However, a process of treating the above oxazolidinone derivatives in contact with water with heating under acidic to neutral conditions and a process of subsequently derivatizing them into β-hydroxyethylamine compounds are included within the present invention, so far as the above N-alkoxycarbonyl-ethylamine compounds are once formed as an intermediate.

Next described is a process of starting from N-alkoxycarbonyl-ethylamine compounds having a leaving group at the β-position to prepare oxazolidinone derivatives of β-hydroxyethylamine compounds which is the first invention of the present inventions.

The first invention comprises two steps which are a step of converting the N-alkoxycarbonyl-ethylamine compounds having a leaving group at the β-position into the oxazolidinone derivatives of β-hydroxyethylamine compounds having an inverted steric configuration at the β-position carbon by heat treatment, acid treatment or base treatment (hereinafter, also referred to as inversion step), as well as, a step of treating in contact with water with heating under acidic to neutral conditions (hereinafter, also referred to as water treatment step). The latter water treatment step is a key step of the present invention for making the components responsible for impurities secondarily produced when the oxazolidinone derivatives of β-hydroxyethylamine compounds are contacted with a base harmless.

The combination of the inversion step and the water treatment step includes the following two embodiments:

the first embodiment: converting the N-alkoxycarbonyl-ethylamine compounds having a leaving group at the β-position into the oxazolidinone derivatives of β-hydroxyethylamine compounds having an inverted steric configuration at the β-position carbon by heat treatment, acid treatment, or base treatment under non-aqueous conditions, and then carrying out a step of treating in contact with water with heating under acidic to neutral conditions (i.e. embodiment sequentially carrying out the inversion step and the water treatment step); and the second embodiment: converting the N-alkoxycarbonyl-ethylamine compounds having a leaving group at the β-position into the oxazolidinone derivatives of β-hydroxyethylamine compounds having an inverted steric configuration at the β-position carbon by heat treatment or acid treatment, and simultaneously carrying out a step of treating in contact with water with heating under acidic to neutral conditions (i.e. embodiment simultaneously carrying out the inversion step and the water treatment step).

Firstly described is the above first embodiment. The inversion step and the water treatment step are sequentially carried out in this embodiment, and the inversion step is firstly described.

The inversion step in the first embodiment can be carried out by a heat treatment, an acid treatment, or a base treatment.

The temperature of carrying out the inversion step by a heat treatment is not limited to a particular range, and is preferably above about 40° C., more preferably above about 60° C., and most preferably above about 80° C. In general, as the reaction temperature becomes higher, the reaction proceeds more rapidly. The upper limit of the reaction temperature is not limited to a particular point if it is below the boiling point of the reaction mixture.

In this inversion step, an acid treatment or a base treatment may be carried out for the purpose of promoting the reaction, if necessary, by coexistence or addition of a suitable amount of an acidic substance or a basic substance. This treatment allows the reaction to proceed rapidly at a lower temperature, and therefore, it is possible to carry out the inversion step at a milder treating temperature or a far milder treating temperature. The treating temperature in this case is preferably below about 40° C., and it is also possible to carry out the step at a temperature below about 20° C. It is particularly preferable to carry out the step in the coexistence of an acidic substance, because it has a high effect of promoting the reaction and it allows a later water treatment step to be carried out easily under acidic to neutral conditions.

The acidic substance is not limited to a particular one organic acids include, for example, sulfonic acids such as methanesulfonic acid, ethanesulfonic acid, p-toluenesulfonic acid, o-, p- or m-nitrobenzenesulfonic acid; carboxylic acids such as formic acid, acetic acid, trifluoroacetic acid, or benzoic acid. Inorganic acids include, for example, hydrochloric acid, sulfuric acid, sulfurous acid, phosphoric acid or the like. The amount of the acidic substance used is not limited to a particular range, and they are usually used in a molar amount of 0.01 to 100-fold, preferably in a molar amount of 0.05 to 50-fold, and more preferably in a molar amount of 0.1 to 20-fold, for example, relative to the N-alkoxycarbonyl-ethylamine compounds.

Also, the basic substance is not limited to a particular one, and weak bases are preferably used. The weak bases are not limited to particular ones. In general, bases showing a pKa value below 10, for example, of the conjugate acid in an aqueous solution are preferably used, and especially, those showing a pKa value below 5 are more preferably used. Specific examples include, for example, amines such as triethylamine, diisopropylamine or pyridine; carbonates such as sodium carbonate or potassium carbonate; hydrogen carbonates such as sodium hydrogen carbonate or potassium hydrogen carbonate organic solvents showing a weak basicity such as N,N-dimethylformamide or the like are also within a range of selection. The amount of the basic substance used is not limited to a particular range, and they are usually used in a molar amount of 0.01 to 100-fold, preferably in a molar amount of 0.05 to 50-fold, and more preferably in a molar amount of 0.1 to 20-fold, for example, relative to the N-alkoxycarbonyl-ethylamine compounds.

If necessary, the acidic substance or basic substance coexisting in or added to the above reaction mixture can be removed by a conventional method after completion of the reaction.

Reaction solvents used in this step are not limited to particular ones, and various solvents usually used may be used. Examples of the reaction solvents include, for example, aliphatic hydrocarbons such as hexane or heptane; aromatic hydrocarbons such as toluene or xylene; halogenated hydrocarbons such as methylene chloride or chloroform; ethers such as tetrahydrofuran, 1,4-dioxane or t-butyl methyl ether; aliphatic acid esters such as methyl acetate, ethyl acetate or isopropyl acetate; aprotic polar solvents such as acetonitrile, N,N-dimethylformamide or dimethyl sulfoxide; alcohols such as methanol, ethanol, isopropanol or benzyl alcohol. Among others, aromatic hydrocarbons, ethers or aliphatic acid esters are preferably used. Toluene is a particularly preferable aromatic hydrocarbon, 1,4-dioxane is a particularly preferable ether, and ethyl acetate is a particularly preferable aliphatic acid ester. These solvents may be used alone or in a mixture of two or more solvents. Besides, if the above acidic substance or basic substance is liquid at the above reaction temperature, the above acidic substance or basic substance may be used so as to also serve as a reaction solvent.

The treating time in this step can not be defined uniformly because it varies depending on the kind of N-alkoxycarbonyl-ethylamine compounds having a leaving group at the β-position, the treating process and the like. However, the treatment can be usually completed within 60 hours, preferably within 24 hours, and more preferably within 12 hours. The treating time can be determined by a simple experiment.

The yield in this step can be expected to be usually above 95%, preferably above 97%, and more preferably above 98%.

In this step, the steric configuration at the β-position carbon is substantially inverted. If the above $R^7$ and $R^8$ differ from each other, the β-position carbon is an asymmetric carbon, and therefore, the steric configuration at the β-position carbon is apparently inverted. However, if the above $R^7$ and $R^8$ independently represent a completely identical organic group, or taken together, represent a divalent organic group completely symmetrical with respect to the β-position carbon, there is no apparent change when the steric configuration at the β-position carbon is substantially inverted.

In this embodiment, a by-product represented by the following general formula (4):

wherein, L and $R^0$ are as defined above, is secondarily produced in the above inversion step, the by-product consisting of the above leaving group (L) and the monovalent organic group ($R^0$) in the above alkoxycarbonyl group. Since the by-product may serve as a certain alkylating agent, an impurity in which a hydrogen atom on a nitrogen atom is substituted with the monovalent organic group ($R^0$) in the alkoxycarbonyl group may be secondarily produced.

When the oxazolidinone derivatives of β-hydroxyethylamine compounds synthesized in the above inversion step are subjected to a further derivatization under basic conditions, more particularly, when they are derivatized into the β-hydroxyethylamine compounds by treating in contact with water under basic conditions, for example, a N-substituted-β-hydroxyethylamine compound represented by the following general formula (5):

wherein, $R^{13}$ represents $R^1$, or a group derived from $R^1$;
$R^{14}$ represents $R^2$, or a group derived from $R^2$;
$R^{15}$ represents $R^3$, or a group derived from $R^3$;
$R^{16}$ represents $R^4$, or a group derived from $R^4$;
$R^0$, $R^1$, $R^2$, $R^3$ and $R^4$ are as defined above; is secondarily produced as an impurity, and the yield of the β-hydroxyethylamine compounds tends to be decreased.

Accordingly, in order to minimize the impurity secondarily produce when the oxazolidinone derivatives of β-hydroxyethylamine compounds are subjected to a further derivatization under basic conditions and to carry out the derivatization in a high yield, it is preferable in the present invention to make the by-product, which coexists in the reaction mixture containing the oxazolidinone derivatives of β-hydroxyethylamine compounds obtained by the above inversion step and may be serve as the above alkylating agent, harmless, for example, by decomposing or removing the by-product. Among others, a process of making the by-product, which may be serve as the above alkylating agent, harmless by hydrolysis is most convenient and efficient, and particularly preferable as a production process which is economically advantageous and is suitable for an industrial production. Accordingly, in this embodiment, the oxazolidinone derivatives of β-hydroxyethylamine compounds synthesized in the above inversion step are subjected to a step of treating in contact with water under acidic to neutral conditions (water treatment step), without isolating and/or purifying them in a pure form by distillation, crystallization or the like.

Next described is the water treatment step in the above first embodiment.

Water used in this step is required to make the above by-product responsible for impurities secondarily produced when the above oxazolidinone derivatives of β-hydroxyethylamine compounds are contacted with a base harmless. The amount of water used in this step is not limited to a particular range, and it is usually used in a molar amount above 5-fold, preferably in a molar amount above 10-fold, more preferably in a molar amount above 20-fold, and most preferably in a molar amount above 50-fold, relative to the N-alkoxycarbonyl-ethylamine compounds having a leaving group at the β-position used in the above inversion step. In general, as the amount of water used becomes larger, the effects of the water treatment become larger and the duration required for the treatment may be shortened. In this connection, from the viewpoint of productivity, water is usually used in a molar amount below 1000-fold, preferably in a molar amount below 500-fold, and more preferably in a molar amount below 100-fold, although there is no problem even if too large amount of water is used.

The treating temperature in this step is not limited to a particular range if the temperature is below the boiling point of the reaction mixture. In general, as the temperature becomes higher, the effects of the water treatment become larger and the duration required for the treatment may be shortened. The treating temperature varies depending on various conditions such as the kind of oxazolidinone derivatives of β-hydroxyethylamine compounds, the amount of water used for the contact, the duration of the contact with water, the acidity of the reaction mixture or the like, and therefore, it can not be defined uniformly. The temperature may be preferably above about 40° C., more preferably above about 60° C., and most preferably above about 80° C.

This step is carried out under acidic to neutral conditions. In general, as the acidity becomes higher, the effects of the water treatment become larger and the duration for the treatment required in this step may be shortened. The above contact is usually carried out under acidic to neutral conditions, preferably under acidic conditions, and more preferably under strongly acidic conditions. Also, this step may be preferably carried out by shifting from neutral conditions to acidic conditions gradually with the progress of the reaction.

This step may be preferably carried out in the coexistence of an acidic substance, if necessary, in order to sift the reaction under acidic to neutral conditions, preferably under acidic conditions, and more preferably under strongly acidic conditions, and/or, in order to maintain the reaction under acidic to neutral conditions, preferably under acidic conditions, and more preferably under strongly acidic conditions. The acidic substance is not limited to a particular one. For example, organic acids include sulfonic acids such as methanesulfonic acid, ethanesulfonic acid, p-toluenesulfonic acid, o-, p- or m-nitrobenzenesulfonic acid; carboxylic acids such as formic acid, acetic acid, trifluoroacetic acid or benzoic acid, and inorganic acids include hydrochloric acid, sulfuric acid, phosphoric acid or the like. The amount of the acidic substance used is not limited to a particular range, and they are usually used in a molar amount of 0.01 to 100-fold, preferably in a molar amount of 0.05 to 50-fold, and more preferably in a molar amount of 0.1 to 20-fold, for example, relative to the N-alkoxycarbonyl-ethylamine compounds having a leaving group at the β-position used in the above inversion step.

In this connection, if the acidity in this step is expressed using a pH value as an indicator (standard), the acidic to neutral conditions refer to usually a range below pH 9, preferably a range below pH 8, and more preferably a range below pH 7. Also, the acidic conditions refer to a range below pH 4 and the strongly acidic conditions refer to a range below pH 2.

Reaction solvents used in this step are not limited to particular ones, and various solvents usually used and exemplified as the reaction solvents used in the above inversion step may be used. In general, the reaction solvents used in the above inversion step are conveniently and generally used as they are.

The treating time in this step can not be defined uniformly because it varies depending on various conditions such as the kind of N-alkoxycarbonyl-ethylamine compounds having a leaving group at the β-position or the kind of oxazolidinone derivatives of β-hydroxyethylamine compounds, the amount of water used for the contact, the treating temperature, the acidity of the reaction mixture or the like. The treatment usually requires 1 or more hours, and particularly 5 or more hours. The treatment can be usually completed within 60 hours, preferably within 24 hours, and more preferably within 12 hours. The treating time can be determined by a simple experiment.

Next described is the above second embodiment. This embodiment is that of converting the N-alkoxycarbonyl-ethylamine compounds having a leaving group at the β-position into the oxazolidinone derivatives of β-hydroxyethylamine compounds having an inverted steric configuration at the β-position carbon by heat treatment or acid treatment, and simultaneously treating in contact with water with heating under acidic to neutral conditions. Thus, this embodiment is that of carrying out the inversion step and the water treatment step simultaneously, so to speak, that to be referred to as an inversion-water treatment step.

In the second embodiment as well, the steric configuration at the β-position carbon is substantially inverted, as in the above first embodiment, when converting the N-alkoxycarbonyl-ethylamine compounds into the oxazolidinone derivatives of β-hydroxyethylamine compounds. If the above $R^7$ and $R^8$ differ from each other, the β-position carbon is an asymmetric carbon, and therefore, the steric configuration at the β-position carbon is apparently inverted. However, if $R^7$ and $R^8$ independently represent a completely identical organic group, or taken together, represent a divalent organic group completely symmetrical with respect to the β-position carbon, there is no apparent change when the steric configuration at the β-position carbon is substantially inverted.

Water used in the second embodiment is required to make the above by-product responsible for impurities secondarily produced when the above oxazolidinone derivatives of β-hydroxyethylamine compounds are contacted with a base harmless. The amount of water used in this step is not limited to a particular range, and it is usually used in a molar amount above 5-fold, preferably in a molar amount above 10-fold, more preferably in a molar amount above 20-fold, and most preferably in a molar amount above 50-fold, relative to the N-alkoxycarbonyl-ethylamine compounds having a leaving group at the β-position. In general, as the amount of water used becomes larger, the effects of the water treatment become larger and the duration required for the treatment may be shortened. In this connection, from the viewpoint of productivity, water is usually used in a molar amount below 1000-fold, preferably in a molar amount below 500-fold, and more preferably in a molar amount below 100-fold, although there is no problem even if too large amount of water is used.

The treating temperature in the second embodiment is not limited to a particular range if the temperature is below the boiling point of the reaction mixture. In general, as the temperature becomes higher, the effects of the water treatment become larger and the duration required for the treatment may be shortened. The treating temperature varies depending on various conditions such as the kind of N-alkoxycarbonyl-ethylamine compounds, the amount of water used for the contact, the duration of the contact with water, the acidity of the reaction mixture or the like, and therefore, it can not be defined uniformly. The temperature may be preferably above about 40° C., more preferably above about 60° C., and most preferably above about 80° C.

The second embodiment is carried out under acidic to neutral conditions. In general, as the acidity becomes higher, the effects of the water treatment become larger and the duration for the treatment required in this embodiment may be shortened. The above contact is usually carried out under acidic to neutral conditions, preferably under acidic conditions, and more preferably under strongly acidic conditions. Also, this embodiment may be preferably carried out by shifting from neutral conditions to acidic conditions gradually with the progress of the reaction.

The second embodiment may be preferably carried out in the coexistence of an acidic substance, if necessary, in order to shift the reaction under acidic to neutral conditions, preferably under acidic conditions, and more preferably under strongly acidic conditions, and/or, in order to maintain the reaction under acidic to neutral conditions, preferably under acidic conditions, and more preferably under strongly acidic conditions. The acidic substance is not limited to a particular one. For example, organic acids include sulfonic acids such as methanesulfonic acid, ethanesulfonic acid, p-toluenesulfonic acid, o-, p- or m-nitrobenzenesulfonic acid; carboxylic acids such as formic acid, acetic acid, trifluoroacetic acid or benzoic acid, and inorganic acids include hydrochloric acid, sulfuric acid, phosphoric acid or the like. The amount of the acidic substance used is not limited to a particular range, and they are usually used in a molar amount of 0.01 to 100-fold, preferably in a molar amount of 0.05 to 50-fold, and more preferably in a molar amount of 0.1 to 20-fold, for example, relative to the N-alkoxycarbonyl-ethylamine compounds having a leaving group at the β-position.

In this connection, if the acidity in the second embodiment is expressed using a pH value as an indicator (standard), the acidic to neutral conditions refer to usually a range below pH 9, preferably a range below pH 8, and more preferably a range below pH 7. Also, the acidic conditions refer to a range below pH 4 and the strongly acidic conditions refer to a range below pH 2.

Reaction solvents used in the second embodiment are not limited to particular ones, and various solvents usually used may be used. Examples of the reaction solvents include aliphatic hydrocarbons such as hexane or heptane; aromatic hydrocarbons such as toluene or xylene; halogenated hydrocarbons such as methylene chloride or chloroform; ethers such as tetrahydrofuran, 1,4-dioxane or t-butyl methyl ether; aliphatic acid esters such as methyl acetate, ethyl acetate or isopropyl acetate; aprotic polar solvents such as acetonitrile, N,N-dimethylformamide or dimethyl sulfoxide; alcohols such as methanol, ethanol, isopropanol or benzyl alcohol; and water. Among others, aromatic hydrocarbons, ethers or aliphatic acid esters are preferably used. Toluene is a particularly preferable aromatic hydrocarbon, 1,4-dioxane is a particularly preferable ether, and ethyl acetate is a particularly preferable aliphatic acid ester. These solvents may be used alone or in a mixture of two or more solvents. Besides, if the above acidic substance is liquid at the above reaction temperature, the above acidic substance may be used so as to also serve as a reaction solvent.

The treating time in the second embodiment can not be defined uniformly because it varies depending on various conditions such as the kind of N-alkoxycarbonyl-ethylamine compounds having a leaving group at the β-position, the amount of water used for the contact, the treating temperature, the acidity of the reaction mixture or the like. The treatment usually requires 1 or more hours, and particularly 5 or more hours. The treatment can be usually completed within 60 hours, preferably within 24 hours, and more preferably within 12 hours. The treating time can be determined by a simple experiment.

In the above second embodiment, the existence of a reaction accelerator is required because the duration required for the inversion step tends to be longer. However, if the reaction accelerator is used, an extra work-up is necessary after the reaction. Accordingly, the above first embodiment is more preferable for the first invention.

In this connection, of course, the step of treating in contact with water (water treatment step) in the above first and second embodiments can be carried out in combination with various procedures such as reflux, concentration, solvent-replacement, distillation, crystallization, extraction and the like, freely without any limitation, so far as the above preferable treating temperature is maintained.

When the oxazolidinone derivatives of β-hydroxyethylamine compounds obtained by the above first invention are subjected to a further derivatization under basic conditions, the secondary production of impurities is inhibited and they can be derivatized in a high quality and a high yield. It is possible to prepare β-hydroxyethylamine compounds in a high quality and a high yield, for example, by treating the oxazolidinone derivatives of β-hydroxyethylamine compounds in contact with water under basic conditions (hydrolyzing).

In the first invention, the yield from the N-alkoxycarbonyl-ethylamine compounds having a leaving group at the β-position to the oxazolidinone derivatives of β-hydroxyethylamine compounds can be expected to be usually above 90%, preferably above 95%, and more preferably above 97%.

Next described is a process of starting from N-alkoxycarbonyl-ethylamine compounds having a leaving group at the β-position to prepare β-hydroxyethylamine compounds in a high quality and a high yield, which is the second invention of the present inventions.

The second invention includes a step of subjecting the N-alkoxycarbonyl-ethylamine compounds having a leaving group at the β-position to heat treatment, acid treatment or base treatment (inversion step) and a step of treating in contact with water under acidic to neutral conditions (water treatment step) in the above first invention, and furthermore, a step of treating in contact with water under basic conditions (hereinafter, also referred to as hydrolysis step).

The combination of the above three steps includes the following two embodiments:

The first embodiment: after subjecting the N-alkoxycarbonyl-ethylamine compounds having a leaving group at the β-position to heat treatment, acid treatment or base treatment under non-aqueous conditions and then carrying out a step of treating in contact with water with heating under acidic to neutral conditions, i.e. after carrying out the inversion step and the water treatment step sequentially, a step of treating in contact with water under basic conditions is further carried out; and The second embodiment: after subjecting the N-alkoxycarbonyl-ethylamine compounds having a leaving group at the β-position to a step of treating in contact with water with heating under acidic to neutral conditions, i.e. after carrying out the inversion step and the water treatment step simultaneously, a step of treating in contact with water under basic conditions is further carried out.

As to the treating conditions of the inversion step and the water treatment step in the above two embodiments, the above first embodiment follows the first embodiment of the above first invention and the above second embodiment follows the second embodiment of the above first invention. The treating conditions of corresponding steps in the above first invention may be used without any limitation.

In this connection, the oxazolidinone derivatives obtained in the second embodiment of the above first invention may contain, as a side product, N-alkoxycarbonyl-β-hydroxyethylamine compounds, more particularly, N-alkoxycarbonyl-β-hydroxyethylamine compounds represented, for example, by the following general formula (6):

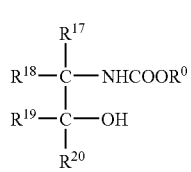

(6)

wherein, $R^{17}$ represents $R^5$, or a group derived from $R^5$; $R^{18}$ represents $R^6$, or a group derived from $R^6$; $R^{19}$ represents $R^7$, or a group derived from $R^7$; $R^{20}$ represents $R^8$, or a group derived from $R^8$; $R^0$, $R^5$, $R^6$, $R^7$ and $R^8$ are as defined above;

which have the same steric configuration as that of the above oxazolidinone derivatives (the content varies depending on the treating conditions). However, the N-alkoxycarbonyl-β-hydroxyethylamine compounds are not problematic in the second invention at all, because they, like the above oxazolidinone derivatives, can be derivatized into the above β-hydroxyethylamine compounds by treating in contact with water under basic conditions.

Next described is the treating conditions of the hydrolysis step in the second invention.

The amount of water used in this step is not limited to a particular range, and it is usually used in a molar amount above 5-fold, preferably in a molar amount above 10-fold, more preferably in a molar amount above 20-fold, and most preferably in a molar amount above 50-fold, relative to the N-alkoxycarbonyl-ethylamine compounds having a leaving group at the β-position. Water may be used in an excess amount, also as a reaction solvent, and usually used so. In this connection, from the viewpoint of productivity, water is usually used in a molar amount below 1000-fold, preferably in a molar amount below 500-fold, and more preferably in a molar amount below 100-fold, although there is no problem even if too large amount of water is used. Of course, water used in the above water treatment step may be used in this step as it is.

In the hydrolysis step, various organic solvents usually used may coexist in a range not affecting the reaction, in addition to water used as a reaction reagent. For example, for the purpose of promotion of the reaction, improvement of the property of the reaction solution or the like, organic solvents having a high dissolubility may be used together. Examples of the various organic solvents include aliphatic hydrocarbons such as hexane or heptane; aromatic hydrocarbons such as toluene or xylene; halogenated hydrocarbons such as methylene chloride or chloroform; ethers such as tetrahydrofuran, 1,4-dioxane or t-butyl methyl ether; aliphatic acid esters such as methyl acetate, ethyl acetate or isopropyl acetate; ketones such as acetone, methyl ethyl ketone or cyclohexanone; aprotic polar solvents such as acetonitrile, N,N-dimethylformamide or dimethyl sulfoxide; alcohols such as methanol, ethanol, isopropanol or benzyl alcohol. Among others, aromatic hydrocarbons or ethers are preferably used. Toluene is a particularly preferable aromatic hydrocarbon and 1,4-dioxane is a particularly preferable ether. These solvents may be used alone or in a mixture of two or more solvents. Of course, the use of these organic solvents includes the case wherein an organic solvent used in the above water-treatment step is used as it is without any solvent-replacement.

This step may be carried out under basic conditions. In general, as the basicity becomes higher, the duration for the treatment required in this step may be shortened. This step is usually carried out under basic conditions, preferably under strongly basic conditions, and more preferably under ultra strongly basic conditions.

In this step, in order to shift the reaction from acidic to neutral conditions in the above water treatment step to basic conditions, and in order to maintain the reaction under basic conditions, the addition of a basic substance is usually and also conveniently and efficiently carried out. The base is not limited to a particular one and strong bases, for example, alkali metal hydroxides such as lithium hydroxide, sodium hydroxide or potassium hydroxide; or alkaline earth metal hydroxides such as magnesium hydroxide or calcium hydroxide are preferably used. Among others, alkali metal hydroxides are preferably used, and especially, lithium hydroxide and sodium hydroxide are preferably used. The amount of the bases used is not limited to a particular range, and they are usually used in a molar amount of 1 to 100-fold, preferably in a molar amount of 2 to 50-fold, and more preferably in a molar amount of 5 to 20-fold, relative to the N-alkoxycarbonyl-ethylamine compounds having a leaving group at the β-position.

In this connection, if the basicity in this step is expressed using a pH value as an indicator (standard), the basic conditions refer to a range above pH 10, the strongly basic conditions refer to a range above pH 12, and the ultra strongly basic conditions refer to a range above pH 14.

The reaction temperature of this step is preferably above about 40° C., more preferably above about 60° C., and most preferably above about 80° C. In general, as the reaction temperature becomes higher, the reaction proceeds more rapidly. The upper limit of the reaction temperature is not limited to a particular point if it is below the boiling point of the reaction mixture.

The treating time in this step can not be defined uniformly because it varies depending on various conditions such as the kind of N-alkoxycarbonyl-ethylamine compounds having a leaving group at the β-position, the amount of water used for the contact, the treating temperature, the basicity of the reaction mixture or the like. The treatment usually requires 1 or more hours, and particularly 5 or more hours. The treatment can be usually completed within 60 hours, preferably within 24 hours, and more preferably within 12 hours. The treating time can be determined by a simple experiment.

The β-hydroxyethylamine compounds synthesized as described above are essentially β-hydroxyethylamine compounds having a high quality, excepting containing secondarily produced salts and reaction solvents, for example, because the secondary production of impurities can be highly inhibited by a series of procedures according to the present invention. Accordingly, they can be suitably and sufficiently used without any isolation in a subsequent derivatization and the like. Also, even if it is preferable to carry out the isolation, the β-hydroxyethylamine compounds having a high quality can be isolated in a relatively convenient manner.

In the second invention, the yield from the N-alkoxycarbonyl-ethylamine compounds having a leaving group at the β-position to the β-hydroxyethylamine compounds can be expected to be usually above 90%, preferably above 95%, and more preferably above 97%.

EXAMPLES

The present invention is illustrated in more detail based on the following examples, reference examples and comparative examples. The present invention is not limited to these examples.

Reference Example 1

Synthesis of (2S,3S)-3-(ethoxycarbonyl)-amino-2-hydroxy-4-phenylbutyric Acid (erythro-isomer)

A toluene solution (677.2 g) containing (S)-1,1-dibromo-3-(ethoxycarbonyl)amino-2-oxo-4-phenylbutane (67.65 g) was added dropwise to a 10% aqueous solution of sodium hydroxide (691.3 g) ice-cooled over 10 hours, and stirred at the same temperature for 1 hour. The resultant reaction solution was further stirred at 60° C. for 6 hours to continue the reaction. The organic phase was separated from the resultant reaction mixture, ethyl acetate (400 ml) was added to the resultant aqueous phase, and the pH was adjusted to pH 2 with conc. hydrochloric acid (150 g). The resultant organic phase was separated to obtain an aqueous solution (944.7 g) containing erythro-3-amino-2-hydroxy-4-phenyl-butyric acid (26.52 g) and threo-3-amino-2-hydroxy-4-phenylbutyric acid (5.44 g). The ratio of erythro-isomer/threo-isomer was 83/17, and the diastereomer excess was 66% d.e.

The aqueous solution (940.4 g) thus obtained [containing erythro-3-amino-2-hydroxy-4-phenylbutyric acid (26.40 g) and threo-3-amino-2-hydroxy-4-phenylbutyric acid (5.42 g)] was adjusted to pH 10 with a 30% aqueous solution of sodium hydroxide (91 g) under ice-cooling. While the aqueous solution was maintained at around pH 10 with a 30% aqueous solution of sodium hydroxide and at an internal temperature below 5° C., ethyl chloroformate (19.52 g) was added dropwise to the solution over 3 hours. The mixture was further stirred at the same temperature for 1 hour to continue the reaction. The reaction solution was warmed to room temperature and washed with toluene (64 ml). Then, ethylacetate (849.3 ml) was added to the solution, the pH was adjusted to pH 2 with conc. hydrochloric acid (60 g), and the aqueous phase was separated. Then, the resultant organic phase was washed with water (96 ml) to obtain an ethyl acetate extract (971.9 g). Determination by HPLC revealed that the amount of the diastereomer mixture of 3-(ethoxycarbonyl)-amino-2-hydroxy-4-phenylbutyric acid in the resultant extract was 43.07 g calculated as an erythro-isomer. Also, the HPLC area ratio of erythro-isomer/threo-isomer was 83/17, and the diastereomer excess was 66% d.e.

The ethyl acetate extract (870.3 g) thus obtained [containing a diastereomer mixture (38.57 g) of 3-(ethoxycarbonyl)amino-2-hydroxy-4-phenylbutyric acid] was concentrated under reduced pressure, and solvent-replacement was then carried out with toluene to precipitate crystals. After the total amount of the concentrate was adjusted to 770.5 g, acetonitrile (118.3 g) was added to the mixture, and the mixture was heated to 70° C. to completely dissolve the crystals. After maintaining the mixture at the same temperature for 1 or more hours, crystallization was carried out by cooling the mixture at a cooling rate of 10° C./hour, and precipitated crystals were separated by suction filtration. The crystals were washed with cold toluene (200 ml) and then dried in vacuo to obtain white crystals (30.23 g). The purity of (2S,3S)-3-(ethoxycarbonyl)amino-2-hydroxy-4-phenylbutyric acid was 99% by weight. Also, the HPLC area ratio of erythro-isomer/threo-isomer was 99/1, and the diastereomer excess was 99% d.e. (2R,3R)-Isomer (enantiomer) was not detected.

Reference Example 2

Synthesis of a Diastereomer Mixture of 3-(ethoxycarbonyl)amino-2-hydroxy-4-phenylbutyric acid The ethylacetate extract (96.5 g) obtained in Reference example 1 [containing a diastereomer mixture (4.28 g) of 3-(ethoxycarbonyl)amino-2-hydroxy-4-phenylbutyric acid; HPLC area ratio of erythro-isomer/threo-isomer=83/17] was concentrated to dry up under reduced pressure. The solid was ground in a porcelain mortar and then further dried in vacuo to obtain a powdery solid (4.43 g). The purity of erythro-3-(ethoxycarbonyl)amino-2-hydroxy-4-phenylbutyric acid was 78% by weight. Also, the HPLC area ratio of erythro-isomer/threo-isomer was 83/17, and the diastereomer excess was 66% d.e.

Reference Example 3

Synthesis of (2S,3S)-3-(t-butoxycarbonyl)-amino-2-hydroxy-4-phenylbutyric acid (erythro-isomer)

(S)-1,1-Dibromo-3-(t-butoxycarbonyl)amino-2-oxo-4-phenylbutane (42.12 g) was suspended in toluene (420 ml) and water (280 ml) and the suspension was ice-cooled. To this suspension, a 30% aqueous solution of sodium hydroxide (133 g) was added dropwise over 1 hour, and the mixture was stirred at the same temperature for 20 hours. The organic phase was separated from the resultant reaction mixture, ethyl acetate (600 ml) was added to the aqueous phase, the pH was adjusted to pH 2 with conc. hydrochloric acid (115 g), and the aqueous phase was separated. Then, the resultant organic phase was washed with water (70 ml) to obtain an ethyl acetate extract (591.9 g). Determination by HPLC revealed that the amount of the diastereomer mixture of 3-(t-butoxycarbonyl) amino-2-hydroxy-4-phenylbutyric acid in the resultant extract was 27.14 g calculated as an erythro-isomer. Also, the HPLC area ratio of erythro-isomer/threo-isomer was 83/17, and the diastereomer excess was 66% d.e.

The ethyl acetate extract (589.2 g) [containing a diastereomer mixture (27.02 g) of 3-(t-butoxycarbonyl) amino-2-hydroxy-4-phenylbutyric acid] was concentrated under reduced pressure, and solvent-replacement was then carried out with toluene to precipitate crystals. After the total amount of the concentrate was adjusted to 544.5 g, acetonitrile (120.3 g) was added to the mixture, and the mixture was heated to 70° C. to completely dissolve the crystals. After maintaining the mixture at the same temperature for 1 hour, crystallization was carried out by cooling the mixture to −10° C. at a cooling rate of 2.5° C./hour, and precipitated crystals were separated by suction filtration. The crystals were washed with cold toluene (150 ml) and then dried in vacuo to obtain white crystals (20.23 g). The purity of (2S,3S)-3-(t-butoxycarbonyl)amino-2-hydroxy-4-phenylbutyric acid was 99% by weight. Also, the HPLC area ratio of erythro-isomer/threo-isomer was 99/1, and the diastereomer excess was 99% d.e. (2R,3R)-Isomer (enantiomer) was not detected.

Example 1

Conversion of (2S, 3S)-3-(ethoxycarbonyl) amino-2-hydroxy-4-phenylbutyric acid into (4S,5R)-4-benzyl-2-oxazolidinone-5-carboxylic acid methyl ester (2S,3 S)-3-(Ethoxycarbonyl) amino-2-hydroxy-4-phenylbutyric acid obtained in Reference example 1 (HPLC area ratio of erythro-isomer/threo-isomer=99/1)(66.87 g) was dissolved in methanol (340 ml) and toluene (300 ml), methanesulfonic acid (2.41 g) was added to the mixture, and the mixture was reacted under reflux for 5 hours. After cooling the resultant reaction solution to room temperature, the pH of the solution was adjusted to pH 6 with a 5% aqueous solution of sodium hydrogencarbonate (42.04 g), and methanol was distilled off under reduced pressure. Ethyl acetate (360 ml) and water (130 ml) were added to the resultant concentrate (330.6 g), the pH was adjusted to pH 8 with a 5% aqueous solution of sodium hydrogencarbonate (12.51 g), and the aqueous phase was separated. The resultant organic phase was then washed with water (130 ml) and concentrated under reduced pressure to obtain an ethyl acetate extract (462.7 g). Determination by HPLC revealed that the amount of (2S, 3S)-3-(ethoxycarbonyl) amino-2-hydroxy-4-phenylbutyric acid methyl ester in the resultant extract was 68.27 g. Also, the HPLC area ratio of erythro-isomer/threo-isomer was 99/1, and the diastereomer excess was 98% d.e.

To the ethyl acetate extract (450.3 g) thus obtained [containing (2S,3S)-3-(ethoxycarbonyl)amino-2-hydroxy-4-phenylbutyric acid methyl ester (66.44 g)], triethylamine (33.46 g) was added under ice-cooling, methanesulfonyl chloride (32.46 g) was then added over 2 hours, and the mixture was reacted at the same temperature for 1 hour. Water (660 ml) was added to the resultant reaction solution, and the aqueous phase was separated. The resultant organic phase was then washed with water (330 ml), ethyl acetate was distilled off under reduced pressure, and solvent-replacement was carried out with toluene. The resultant solvent-replaced solution was reacted at 110° C. for 12 hours to obtain a toluene solution (668.5 g). Determination by HPLC revealed that the amount of (4S,5R)-4-benzyl-2-oxazolidinone-5-carboxylic acid methyl ester in the resultant toluene solution was 54.39 g. Also, the HPLC area ratio of threo-isomer/erythro-isomer was 99/1, and the diastereomer excess was 99% d.e.

Example 2

Conversion of (2S,3S)-3-(ethoxycarbonyl)amino-2-methanesulfonyloxy-4-phenylbutyric acid methyl ester into (2R,3S)-3-amino-2-hydroxy-4-phenylbutyric acid via inversion reaction in the coexistence of water To the ethyl acetate extract (10.17 g) of (2S,3S)-3-(ethoxycarbonyl)amino-2-hydroxy-4-phenylbutyric acid methyl ester obtained in Example 1 [containing (2S,3S)-3-(ethoxycarbonyl)amino-2-hydroxy-4-phenylbutyric acid methyl ester (1.50 g); HPLC area ratio of erythro-isomer/threo-isomer=99/1], triethylamine (756 mg) was added under ice-cooling, methanesulfonyl chloride (733 mg) was then added over 10 minutes, and the mixture was reacted at the same temperature for 2 hours. Water (15 ml) was added to the resultant reaction solution, and the aqueous phase was separated. The resultant organic phase was then washed with water (8 ml), ethyl acetate was distilled off under reduced pressure, and solvent-replacement was carried out with toluene to obtain a solvent-replaced solution (7.59 g). Water (1.5 ml) and N,N-dimethylformamide (5.98 g) were added to the solution (pH 9). The mixture was reacted at 85° C. for 12 hours. The pH of the resultant reaction solution (14.88 g) was pH 4. Determination by HPLC of the reaction solution thus obtained revealed that the content of (4S,5R)-4-benzyl-2-oxazolidinone-5-carboxylic acid methyl ester in the reaction solution was 0.35 g and that of (2R,3S)-3-(ethoxycarbonyl)-amino-2-hydroxy-4-phenylbutyric acid methyl ester was 1.04 g. When combining these two inversion products, the HPLC area ratio of threo-isomer/erythro-isomer was 99/1, and the diastereomer excess was 98% d.e.

The reaction solution (14.05 g) thus obtained [containing (4S,5R)-4-benzyl-2-oxazolidinone-5-carboxylic acid methyl ester (0.33 g) and (2R,3S)-3-(ethoxycarbonyl)-amino-2-hydroxy-4-phenylbutyric acid methyl ester (0.98 g)] was concentrated under reduced pressure, and solvent-replacement was carried out with toluene. Insoluble matters were filtered off, water (5 ml) and a 30% aqueous solution of sodium hydroxide (6.61 g) were added to the resultant toluene solution, and the mixture was reacted at 60° C. for 12 hours with stirring. The organic phase was separated from the resultant reaction solution (pH 14), water (2 ml) was added to the organic phase, and the mixture was throughly mixed at 60° C. with stirring. The resultant aqueous phase was separated and collected together with the previous aqueous phase. Determination by HPLC of the aqueous phase thus obtained revealed that the content of (2R,3S)-3-amino-2-hydroxy-4-phenylbutyric acid in the aqueous phase was 0.95 g, the yield was 97%, and the purity was 99%(area percent method). Also, the HPLC area ratio of threo-isomer/erythro-isomer was 99/1, and the diastereomer excess was 99% d.e.

Example 3

Purification of (4S,5R)-4-benzyl-2-oxazolidinone-5-carboxylic acid methyl ester

The toluene solution (66.9 g) obtained in Example 1 [containing (4S,5R)-4-benzyl-2-oxazolidinone-5-carboxylic acid methyl ester (5.44 g); HPLC area ratio of threo-isomer/erythro-isomer=99/1] was concentrated under reduced pressure to obtain an oily substance (7.79 g). Toluene was added to the oily substance up to the amount of 54.7 g, and the substance was again dissolved by stirring at 70° C. for 3 hours. When the toluene solution was cooled and then stirred for 3 days, it was found that crystals precipitated from the solution. The solution was further cooled to −10° C., and precipitated crystals were separated by suction filtration. The crystals were washed with cold toluene (150 ml) and then dried in vacuo to obtain purified (4S,5R)-4-benzyl-2-oxazolidinone-5-carboxylic acid methyl ester (5.06 g) as white crystals. The purity of (4S,5R)-4-benzyl-2-oxazolidinone-5-carboxylic acid methyl ester was 99% (area percent method). Also, the HPLC area ratio of threo-isomer/erythro-isomer was 99/1, and the diastereomer excess was 99% d.e.

$^1$H-NMR. Spectra (CDCl$_3$, TMS internal standard) of the resultant (4S,5R)-4-benzyl-2-oxazolidinone-5-carboxylic acid methyl ester were: δ 2.79 (1H, dd, CH$_2$Ph, J=13.2 Hz (CH$_2$Ph), 10 Hz (H-4)), 3.07 (1H, dd, CH$_2$Ph, J=13.2 Hz (CH$_2$Ph), 4.4 Hz (H-4)), 3.86 (3H, s, CO$_2$CH$_3$), 4.01-4.09 (1H, m, H-4), 4.72 (1H, d, H-5, J=4.4 Hz (H-4)), 7.15-7.38 (5H, m, Ph).

On the other hand, the crystallization mother liquor and the toluene washing were combined, and the resultant solution was concentrated under reduced pressure to remove toluene. The residue was further dried in vacuo to obtain methanesulfonic acid ethyl ester (2.69 g) as an oily substance.

$^1$H-NMR Spectra (CDCl$_3$, TMS internal standard) of the resultant methanesulfonic acid ethyl ester were: δ 0.92 (3H, t, CH$_3$, J=6.8 Hz), 2.23 (3H, s, CH$_3$SO$_2$), 3.77 (2H, q, CH$_2$, J=6.8 Hz).

Example 4

Conversion of Purified (4S,5R)-4-benzyl-2-oxazolidinone-5-carboxylic acid methyl ester into (2R,3S)-3-amino-2-hydroxy-4-phenylbutyric acid Purified (4S,5R)-4-benzyl-2-oxazolidinone-5-carboxylic acid methyl ester (2.35 g) obtained in Example 3 was suspended in toluene (25 ml) and water (10 ml), a 30% aqueous solution of sodium hydroxide (13.33 g) was added to the suspension, and the mixture was reacted at 60° C. for 12 hours with stirring. Determination by HPLC of the resultant reaction solution revealed that the content of (2R, 3S)-3-amino-2-hydroxy-4-phenylbutyric acid in the reaction solution was 1.91 g, the yield was 98%, and the purity was 98% (area percent method). Also, the HPLC area ratio of threo-isomer/erythro-isomer was 99/1, and the diastereomer excess was 99% d.e.

Example 5

Conversion of (4S,5R)-4-benzyl-2-oxazolidinone-5-carboxylic acid methyl ester into (2R,3S)-3-amino-2-hydroxy-4-phenylbutyric acid (with water treatment)

The toluene solution (28.88 g) obtained in Example 1 [containing (4S,5R)-4-benzyl-2-oxazolidinone-5-carboxylic acid methyl ester (2.35 g); HPLC area ratio of threo-isomer/erythro-isomer=99/1; containing methanesulfonic acid ethyl ester] was mixed with water (10 ml), and the mixture was reacted at 80° C. for 12 hours with stirring (pH 1). Analysis by GC of the resultant reaction solution revealed that methanesulfonic acid ethyl ester was not detected in the reaction solution. To the reaction solution, a 30% aqueous solution of sodium hydroxide (13.33 g) was added, and the mixture was reacted at 60° C. for 12 hours with stirring. The organic phase was separated from the resultant reaction solution, and water (5 ml) was added to the organic phase. The mixture was throughly mixed at 60° C. with stirring. The resultant aqueous phase was separated and collected together with the previous aqueous phase. Determination by HPLC of the aqueous phase (30.72 g) thus obtained revealed that the content of (2R,3S)-3-amino-2-hydroxy-4-phenylbutyric acid in the aqueous phase was 1.92 g, the yield was 98%, and the purity was 99% (area percent method). Also, the HPLC area ratio of threo-isomer/erythro-isomer was 99/1, and the diastereomer excess was 99% d.e.

Comparative Example 1

Conversion of (4S,5R)-4-benzyl-2-oxazolidinone-5-carboxylic acid methyl ester into (2R,3S)-3-amino-2-hydroxy-4-phenylbutyric acid (without water treatment)

Firstly, a 30% aqueous solution of sodium hydroxide (13.33 g) was cooled to 50° C. with stirring, and the toluene solution (28.88 g) obtained in Example 1 [containing (4S, 5R)-4-benzyl-2-oxazolidinone-5-carboxylic acid methyl ester (2.35 g); HPLC area ratio of threo-isomer/erythro-isomer=99/1; containing methanesulfonic acid ethyl ester] was added dropwise to the cooled solution over 30 minutes (pH 14). The temperature of the mixture was raised to 60° C., and the mixture was reacted for further 12 hours with stirring. Water (10 ml) was then added to the reaction solution, and the organic phase was separated from the resultant reaction solution. Water (4 ml) was added to the organic phase, and the mixture was throughly mixed at 60° C. with stirring. The aqueous phase was separated and collected together with the previous aqueous phase. Determination by HPLC of the aqueous phase (27.98 g) thus obtained revealed that the content of (2R, 3S)-3-amino-2-hydroxy-4-phenylbutyric acid in the aqueous phase was 1.24 g, the yield was 64%, and the purity was 64% (area percent method). Also, the HPLC area ratio of threo-isomer/erythro-isomer was 99/1, the diastereomer excess was 98% d.e., and the content of (2R, 3S)-3-ethylamino-2-hydroxy-4-phenylbutyric acid secondarily produced was 35% (area percent method).

Comparative Example 2

Conversion of(4S,5R)-4-benzyl-2-oxazolidinone-5-carboxylic acid methyl ester into (2R,3S)-3-amino-2-hydroxy-4-phenylbutyric acid (without water treatment)

The toluene solution (28.88 g) obtained in Example 1 [containing (4S, 5R)-4-benzyl-2-oxazolidinone-5-carboxylic acid methyl ester (2.35 g); HPLC area ratio of threo-isomer/erythro-isomer=99/1; containing methanesulfonic acid ethyl ester] was mixed with water (10 ml), a 30% aqueous solution of sodium hydroxide (13.33 g) was added to the mixture (pH 14), and the mixture was reacted at 60° C. for 12 hours with stirring. The organic phase was separated from the resultant reaction solution, water (4 ml) was added to the organic phase, and the mixture was throughly mixed at 60° C. with stirring. The resultant aqueous phase was separated and collected together with the previous aqueous phase. Determination by HPLC of the aqueous phase thus obtained revealed that the content of (2R, 3S)-3-amino-2-hyddroxy-4-phenylbutyric acid in the aqueous phase was 1.56 g, the yield was 80%, and the purity was 79% (area percent method). Also, the HPLC area ratio of threo-isomer/erythro-isomer was 99/1, the diastereomer excess was 98% d.e., and the content of (2R, 3S)-3-ethylamino-2-hydroxy-4-phenylbutyric acid secondarily produced was 18% (area percent method).

From the above results, it is apparent that water treatment increases the yield and the purity.

Comparative Example 3/Examples 6-7

Conversion of (4S,5R)-4-benzyl-2-oxazolidinone-5-carboxylic Acid Methyl Ester Into (2R,3S)-3-amino-2-hydroxy-4-phenylbutyric acid (with water treatment: effects of water content)

The toluene solution (92.42 g) obtained in Example 1 [containing (4S,5R)-4-benzyl-2-oxazolidinone-5-carboxylic acid methyl ester (7.52 g); HPLC area ratio of threo-isomer/erythro-isomer=99/1] was concentrated and solvent-replaced with 1,4-dioxane to obtain a 1,4-dioxane solution (92.50 g).

The 1,4-dioxane solution (28.89 g) thus obtained [containing (4S,5R)-4-benzyl-2-oxazolidinone-5-carboxylic acid methyl ester (2.35 g); HPLC area ratio of threo-isomer/erythro-isomer=99/1; containing methanesulfonic acid ethyl ester] was mixed with 0.2, 4 and 10 ml of water [molar amounts of 1-, 20- and 50-fold, respectively, relative to the material used in Example 1, (2S,3S)-3-(ethoxycarbonyl)amino-2-hydroxy-4-phenylbutyric acid methyl ester], and the mixtures were reacted at 60° C. for 48 hours with stirring. To the reaction solutions thus obtained, water was added so as to give a water content of 10 ml, respectively. Then, a 30% aqueous solution of sodium hydroxide (13.33 g) was added to the mixtures, and the mixtures were reacted at 60° C. for 12 hours with stirring. Water (15 ml) was added to each reaction solution separated into two layers to homogenize the reaction solutions. The content, yield, and purity (area percent method) of (2R,3S)-3-amino-2-hydroxy-4-phenylbutyric acid were determined by HPLC. The results are shown in Table 1.

TABLE 1

| | Water content of water treatment | (2R,3S)-3-amino-2-hydroxy-4-phenylbutyric acid | | |
|---|---|---|---|---|
| | | Content | Yield | Purity |
| Comparative example 3 | 0.2 ml | 1.55 g | 79% | 84% |
| Example 6 | 4 ml | 1.81 g | 93% | 95% |
| Example 7 | 10 ml | 1.92 g | 98% | 99% |

From the above results, it is apparent that the increase of the water content leads to the increase of the effects of the water treatment.

Comparative Example 4/Examples 8-10

Conversion of (4S,5R)-4-benzyl-2-oxazolidinone-5-carboxylic Acid Methyl Ester Into (2R,3S)-3-amino-2-hydroxy-4-phenylbutyric acid (effects of duration of water treatment)

The toluene solution (28.88 g) obtained in Example 1 [containing (4S,5R)-4-benzyl-2-oxazolidinone-5-carboxylic acid methyl ester (2.35 g); HPLC area ratio of threo-isomer/erythro-isomer=99/1; containing methanesulfonic acid ethyl ester] was mixed with water (10 ml), and the mixture was reacted at 60° C. for 1, 12, 24 or 48 hours with stirring. To each reaction solution, a 30% aqueous solution of sodium hydroxide (13.33 g) was added, and the mixture was reacted at 60° C. for 12 hours with stirring. The organic phase was separated from the resultant reaction solution, and water (5 ml) was added to the organic phase. The mixture was throughly mixed at 60° C. with stirring. The resultant aqueous phase was separated and collected together with the previous aqueous phase. The content, yield, and purity (area percent method) of (2R,3S)-3-amino-2-hydroxy-4-phenylbutyric acid in the aqueous phase thus obtained were determined by HPLC. The results are shown in Table 2.

TABLE 2

| | Duration of water treatment | (2R,3S)-3-amino-2-hydroxy-4-phenylbutyric acid | | |
|---|---|---|---|---|
| | | Content | Yield | Purity |
| Comparative example 4 | 1 hour | 1.59 g | 82% | 84% |
| Example 8 | 12 hours | 1.83 g | 94% | 95% |
| Example 9 | 24 hours | 1.89 g | 97% | 98% |
| Example 10 | 48 hours | 1.94 g | 99% | 99% |

From the above results, it is apparent that the elongation of the duration leads to the increase of the effects of the water treatment.

Example 11

Water treatment for making methanesulfonic acid Ethyl Ester Contained in (4S,5R)-4-benzyl-2-oxazolidinone-5-carboxylic acid methyl ester reaction solution harmless The toluene solution (reaction solution)(28.88 g) obtained in Example 1 [containing (4S,5R)-4-benzyl-2-oxazolidinone-5-carboxylic acid methyl ester (2.35 g); HPLC area ratio of threo-isomer/erythro-isomer=99/1; containing methanesulfonic acid ethyl ester] was mixed with water (10 ml), and the mixture was reacted at 60° C. with stirring. The reaction solution were sampled at reaction times of 0, 12, 24 and 48 hours. The remaining ratio of methanesulfonic acid ethyl ester in the reaction solution were determined by GC. The results are shown in Table 3.

TABLE 3

| Duration of water treatment | Remaining ratio of methanesulfonic acid ethyl ester (0 hour set to 100%) |
|---|---|
| 0 hour | 100% |
| 12 hours | 28% |
| 24 hours | 10% |
| 48 hours | 2% |

From the above results, it is apparent that methanesulfonic acid ethyl ester is made harmless by the water treatment (by hydrolysis).

Example 12

Crystallization Example of (2R,3S)-3-amino-2-hydroxy-4-phenylbutyric acid

Conc. hydrochloric acid was added in portions at 60° C. to the aqueous phase (29.97 g) obtained in Example 5 [containing (2R,3S)-3-amino-2-hydroxy-4-phenylbutyric acid (1.85 g); HPLC area ratio of threo-isomer/erythro-isomer=99/1], whereby crystals gradually precipitated. The pH was finally adjusted to pH 5. Then, cooling crystallization was carried out at a cooling rate of 5° C./hour, and precipitated crystals were separated by suction filtration. The crystals were washed with cold water (8 ml) and then dried in vacuo to obtain white crystals (1.77 g). The purity of (2R,3S)-3-amino-2-hydroxy-4-phenylbutyric acid (threo-isomer) was 98% by weight, and the water content was 2% by weight. Neither erythro-isomer (diastereomer) nor (2S,3R)-isomer (enantiomer) was detected.

$^1$H-NMR Spectra (D$_2$O, sodium 2,2-dimethyl-2-silapentane-5-sulfonate (DSS) internal standard) of the resultant crystals of (2R,3S)-3-amino-2-hydroxy-4-phenylbutyric acid were: δ 2.95 (1H, dd, H-4, J=14 Hz (H-4), J=8.8 Hz (H-3)), 3.16 (1H, dd, H-4, J=14 Hz (H-4), J=6.8 Hz (H-3)), 3.76-3.83 (1H, m, H-3), 4.06 (1H, d, H-2, J=2.8 Hz (H-3)), 7.35-7.48 (5H, m, Ph).

Also, $^{13}$C NMR spectra (D$_2$O, DSS internal standard) were: δ 38.2, 58.2, 73.4, 130.5, 132.0, 132.3, 138.4, 179.9.

Reference Example 4

Conversion of (4S,5R)-4-benzyl-2-oxazolidinone-5-carboxylic acid methyl ester into (2R,3S)-3-ethylamino-2-hydroxy-4-phenylbutyric acid From the toluene solution (88.73 g) obtained in Example 1 [containing (4S,5R)-4-benzyl-2-oxazolidinone-5-carboxylic acid methyl ester (7.22 g); HPLC area ratio of threo-isomer/erythro-isomer=99/1; containing methanesulfonic acid ethyl ester], toluene was distilled off under reduced pressure, and tetrahydrofuran was then added to the residue to obtain a solvent-replaced solution (90.11 g). The solvent-replaced solution was added dropwise to a suspension of sodium hydride (oily, 60% by weight)(1.48 g) and tetrahydrofuran (15 ml) cooled to 5° C. over 15 minutes. THF (30 ml) was further added to the mixture, and the mixture was reacted at the same temperature for 1 hour. The resultant reaction solution was decanted to remove most of a large quantity of white precipitates. The resultant supernatant solution was further filtrated to remove insoluble matters. The solvent of the filtrate was distilled off under reduced pressure, and the residue was dried in vacuo to obtain an oily substance (3.94 g).

Water (30 ml) and a 30% aqueous solution of sodium hydroxide (30.42 g) were added to the oily substance (3.35 g) thus obtained, and the mixture was reacted at 60° C. for 20 hours. To the resultant reaction solution [containing (2R,3S)-3-amino-2-hydroxy-4-phenylbutyric acid (17%), (2S,3S)-3-amino-2-hydroxy-4-phenylbutyric acid (1%), and secondarily produced (2R,3S)-3-ethylamino-2-hydroxy-4-phenylbutyric acid (76%)(all values by area percent method)], conc. hydrochloric acid was added in portions at 60° C., whereby crystals gradually precipitated. The pH was finally adjusted to pH 5. Then, cooling crystallization was carried out at a cooling rate of 5° C./hour, and precipitated crystals were separated by suction filtration. The crystals were washed with cold water (4 ml) and then dried in vacuo to obtain white crystals (1.18 g). The content of (2R,3S)-3-ethylamino-2-hydroxy-4-phenylbutyric acid was 97% (area percent method).

$^1$H NMR Spectra (D$_2$O—K$_2$CO$_3$, sodium 2,2-dimethyl-2-silapentane-5-sulfonate (DSS) internal standard) of the resultant (2R,3S)-3-ethylamino-2-hydroxy-4-phenylbutyric acid were: δ 1.03 (3H, t, CH$_3$, J=7.1 Hz), 2.63-2.74 (2H, m, CH$_2$), 2.83 (1H, dd, H-4, J=14 Hz (H-4), J=8.8 Hz (H-3)), 2.92 (1H, dd, H-4, J=14 Hz (H-4), J=6.4 Hz (H-3)), 3.35 (1H, m, H-3), 3.85 (1H, d, H-2, J=2.0 Hz (H-3)), 7.30-7.44 (5H, m, Ph).

Also, $^{13}$C NMR spectra (D$_2$O—K$_2$CO$_3$, DSS internal standard) were: δ 16.1, 40.3, 44.0, 63.6, 74.1, 129.5, 131.6, 132.3, 141.6, 167.4.

Reference Example 5

Crystallization Example of a Mixture of (2R,3S)-3-amino-2-hydroxy-4-phenylbutyric acid and (2R,3S)-3-ethylamino-2-hydroxy-4-phenylbutyric acid To the aqueous phase (25.50 g) obtained in Comparative example 1 [containing (2R,3S)-3-amino-2-hydroxy-4-phenylbutyric acid (1.13 g); HPLC area ratio of threo-isomer/erythro-isomer=99/1; containing secondarily produced (2R,3S)-3-ethylamino-2-hydroxy-4-phenylbutyric acid (35%)(area percent method)], water (75 ml) was added and conc. hydrochloric acid was added in portions at 60° C., whereby crystals gradually precipitated. The pH was finally adjusted to pH 5. Then, cooling crystallization was carried out at a cooling rate of 5° C./hour, and precipitated crystals were separated by suction filtration. The crystals were washed with cold water (4 ml) and then dried in vacuo to obtain white crystals (1.07 g). The content of (2R,3S)-3-ethylamino-2-hydroxy-4-phenylbutyric acid was 72% (area percent method).

Signals characteristic of (2R,3S)-3-ethylamino-2-hydroxy-4-phenylbutyric acid as shown in Reference example 4 were confirmed in $^1$H-NMR spectra (D$_2$O-K$_2$CO$_3$, sodium 2,2-dimethyl-2-silapentane-5-sulfonate (DSS) internal standard) of the resultant crystals.

Example 13

Conversion of (2S,3S)-3-(t-butoxycarbonyl)amino-1-chloro-2-hydroxy-4-phenylbutane Into (4S,5R)-5-chloromethyl-4-benzyl-2-oxazolidinone via inversion reaction in the coexistence of water Firstly, (2S,3S)-3-(t-butoxycarbonyl)amino-1-chloro-2-hydroxy-4-phenylbutane (2.50 g) was dissolved in tetrahydrofuran (20 ml). Triethylamine (1.11 g) was added to the solution under ice-cooling, methanesulfonyl chloride (0.99 g) was then added to the mixture over 30 minutes, and the mixture was reacted at the same temperature for 1 hour. The resultant reaction solution was added to water (15 ml), and the pH was adjusted to pH 5 with conc. hydrochloric acid. Ethyl acetate (15 ml) was then added to the mixture, and the mixture was throughly mixed at room temperature with stirring. The resultant aqueous phase was separated, ethyl acetate (15 ml) was added to the aqueous phase, and the mixture was throughly mixed at room temperature with stirring. The resultant organic phase was separated and collected together with the previous organic phase. The resultant organic phase was then washed with water (5 ml), the solvent was distilled off under reduced pressure, and solvent-replacement was carried out with toluene to obtain a solvent-replaced solution (5.56 g). Water (2 ml) and N,N-dimethylformamide (5 ml) were added to the solution (pH 9). The mixture was reacted at 85° C. for 12 hours. The pH of the resultant reaction solution was pH 4. Determination by HPLC of the reaction solution thus obtained revealed that the content of (4S,5R)-1-chloromethyl-4-benzyl-2-oxazolidinone in the reaction solution was 1.69 g.

Example 14

Conversion of (2S,3S)-3-(ethoxycarbonyl)amino-1-chloro-2-hydroxy-4-phenylbutane Into (4S,5R)-5-chloromethyl-4-benzyl-2-oxazolidinone Firstly, (2S,3S)-3-(ethoxycarbonyl)amino-1-chloro-2-hydroxy-4-phenylbutane (2.23 g) was dissolved in tetrahydrofuran (20 ml). Triethylamine (1.10 g) was added to the solution under ice-cooling, methanesulfonyl chloride (1.01 g) was then added to the mixture over 30 minutes, and the mixture was reacted at the same temperature for 1 hour. The resultant reaction solution was added to water (15 ml), and the pH was adjusted to pH 5 with conc. hydrochloric acid. Ethyl acetate (15 ml) was then added to the mixture, and the mixture was throughly mixed at room temperature with stirring. The resultant aqueous phase was separated, ethyl acetate (15 ml) was added to the aqueous phase, and the mixture was throughly mixed at room temperature with stirring. The resultant organic phase was separated and collected together with the previous organic phase. The resultant organic phase was washed with water (5 ml), the solvent was distilled off under reduced pressure, and solvent-replacement was carried out with toluene to obtain a solvent-replaced solution (5.35 g). N,N-Dimethylformamide (15 ml) was added to the solution, and the mixture was reacted at 100° C. for 12 hours. The reaction solution thus obtained was concentrated under reduced pressure to obtain an oily substance (2.68 g). Ethyl acetate (30 ml) and water (15 ml) were added to the oily substance, and the mixture was stirred at 80° C. for 12 hours. The resultant organic phase was separated, and washed twice with water (15 ml). Analysis by GC of the organic phase thus obtained revealed that methanesulfonic acid ethyl ester was not detected in the organic phase. The solvent of the organic phase was distilled off under reduced pressure to obtain (4S,5R)-1-chloromethyl-4-benzyl-2-oxazolidinone (1.69 g) as an oily substance.

$^1$H-NMR Spectra (CDCl$_3$, TMS internal standard) of the resultant (4S,5R)-1-chloromethyl-4-benzyl-2-oxazolidinone were: δ 2.87-2.98 (2H, m, CH$_2$Ph), 3.52 (1H, dd, CH$_2$Cl, J=12 Hz (CH$_2$Cl), 4.4 Hz (H-5)), 3.59 (1H, dd, CH$_2$Cl, J=12 Hz (CH$_2$Cl), 4.9 Hz (H-5)), 3.98 (1H, ddd, H-4, J=6.8 Hz (H-5), J=5.9 Hz (CH$_2$Ph), J=5.4 Hz (CH$_2$Ph)), 4.50 (1H, ddd, H-5, J=6.8 Hz (H-4), J=4.9 Hz (CH$_2$Cl), J=4.4 Hz (CH$_2$Cl)), 5.57 (1H, S, H-3), 7.18-7.38 (5H, m, Ph).

INDUSTRIAL UTILIZATION

As described above, in accordance with the present invention, it is possible to prepare oxazolidinone derivatives of β-hydroxyethylamine compounds suitable for contacting with a base, by converting N-alkoxycarbonyl-ethylamine compounds having a leaving group at the β-position into oxazolidinone derivatives of β-hydroxyethylamine compounds, and making the components responsible for impurities secondarily produced when the above oxazolidinone derivatives are contacted with a base harmless. Also, it is possible to prepare β-hydroxyethylamine compounds in a high quality and a high yield from N-alkoxycarbonyl-ethylamine compounds having a leaving group at the β-position while inhibiting the secondary production of impurities.

The invention claimed is:

1. A process of starting from a N-alkoxycarbonyl-ethylamine compound having a leaving group at the β-position to prepare an oxazolidinone derivative of a β-hydroxyethylamine compound having an inverted steric configuration at the β-position carbon, which comprises:

converting the N-alkoxycarbonyl-ethylamine compound having a leaving group at the β-position into an oxazolidinone derivative of a β-hydroxyethylamine compound having an inverted steric configuration at the β-position carbon under non-aqueous conditions, whereby a by-product L-R$^0$ is secondarily produced from the leaving group (L) and the monovalent organic group (R$^0$) in the alkoxycarbonyl group (—COOR$^0$) present in the N-alkoxycarbonyl-ethylamine, and then carrying out a step of treating in contact with water in a molar amount above 5-fold with heating to above 40° C. under acidic to neutral conditions, whereby the by-product L-R$^0$ is made harmless.

2. In a process of starting from a N-alkoxycarbonyl-ethylamine compound having a leaving group at the β-position to prepare an oxazolidinone derivative of a β-hydroxyethylamine compound having an inverted steric configuration at the β-position carbon, the improvement comprising:

subjecting the N-alkoxycarbonyl-ethylamine compound having a leaving group at the β-position to a step of treating in contact with water in a molar amount above 5-fold with heating to above 40° C. under acidic to neutral conditions.

3. A process of starting from a N-alkoxycarbonyl-ethylamine compound having a leaving group at the β-position to prepare a β-hydroxyethylamine compound having an inverted steric configuration at the β-position carbon, which comprises:

converting the N-alkoxycarbonyl-ethylamine compound having a leaving group at the β-position into an oxazolidinone derivative of a β-hydroxyethylamine compound having an inverted steric configuration at the β-position carbon under non-aqueous conditions, whereby a by-product L-R$^0$ is secondarily produced from the leaving group (L) and the monovalent organic group (R$^0$) in the alkoxycarbonyl group (—COOR$^0$) present in the N-alkoxycarbonyl-ethylamine.

then carrying out a step of treating in contact with water in a molar amount above 5-fold with heating to above 40° C. under acidic to neutral conditions, and then carrying out a step of treating in contact with water under basic conditions, whereby the by-product L-R$^0$ is made harmless.

4. In a process of starting from a N-alkoxycarbonyl-ethylamine compound having a leaving group at the β-position to prepare a β-hydroxyethylamine compound having an inverted steric configuration at the 13-position carbon, the improvement comprising:

subjecting the N-alkoxycarbonyl-ethylamine compound having a leaving group at the β-position to a step of treating in contact with water in a molar amount above 5-fold with heating to above 40° C. under acidic to neutral conditions, and then carrying out a step of treating in contact with water under basic conditions.

5. The process according to claim 1 or 3 wherein the step of converting the N-alkoxycarbonyl-ethylamine compound having a leaving group at the β-position into the oxazolidinone derivative of the β-hydroxyethylamine compound having an inverted steric configuration at the β-position carbon under non-aqueous conditions is carried out with heating to above 40° C.

6. The process according to claim 3 wherein the step of treating in contact with water under basic conditions is carried out with heating to above 40° C.

7. The process according to claim 3 wherein the step of converting the N-alkoxycarbonyl-ethylamine compound having a leaving group at the β-position into the oxazolidinone derivative of the β-hydroxyethylamine compound having an inverted steric configuration at the β-position carbon under non-aqueous conditions is carried out with heating to above 40° C., and the step of treating in contact with water under basic conditions is carried out with heating to above 40° C.

8. The process according to claim 1 wherein the step of treating in contact with water in a molar amount above 5-fold under acidic to neutral conditions is carried out by shifting from neutral conditions to acidic conditions gradually.

9. The process according to claim 1 wherein the step of treating in contact with water in a molar amount above 5-fold under acidic to neutral conditions is carried out under acidic conditions.

10. The process according to claim 1 wherein the step of treating in contact with water in a molar amount above 5-fold under acidic to neutral conditions is carried out under strongly acidic conditions.

11. The process according to claim 1 wherein the step of treating in contact with water in a molar amount above 5-fold under acidic to neutral conditions is carried out in the coexistence of an acidic substance in the same reaction vessel.

12. The process according to claim 1 wherein the leaving group is a sulfonyloxy group.

13. The process according to claim 1 wherein the leaving group is a halosulfinyloxy group.

14. The process according to claim 1 wherein the leaving group is a halogen atom.

15. The process according to claim 1 wherein the N-alkoxycarbonyl-ethylamine compound having a leaving group at the β-position is a 3-(alkoxycarbonyl)amino-2-(leaving group)-4-phenylbutyric acid, the oxazolidinone derivative of the β-hydroxyethylamine compound having an inverted steric configuration at the β-position carbon is a 4-benzyl-5-carboxy-2-oxazolidinone derivative, and the β-hydroxyethylamine compound having an inverted steric configuration at the β-position carbon is 3-amino-2-hydroxy-4-phenylbutyric acid.

16. The process according to claim 1 wherein the N-alkoxycarbonyl-ethylamine compound having a leaving group at the β-position is a 3-(alkoxycarbonyl)amino-1-chloro-2-(leaving group)-4-phenylbutane, the oxazolidinone derivative of the β-hydroxyethylamine compound having an inverted steric configuration at the β-position carbon is a 4-benzyl-5-chloromethyl-2-oxazolidinone derivative, and the β-hydroxyethylamine compound having an inverted steric configuration at the β-position carbon is a 3-amino-1-chloro-2-hydroxy-4-phenylbutane derivative.

17. The process according to claim 1 wherein the alkoxycarbonyl group is a lower alkoxycarbonyl group having 1 to 4 carbon atoms, or a substituted or unsubstituted aralkyloxycarbonyl group having 7 to 10 carbon atoms.

\* \* \* \* \*